United States Patent [19]
Toot, Jr. et al.

[11] Patent Number: 5,578,173
[45] Date of Patent: Nov. 26, 1996

[54] REMOVAL OF DIMETHYLTEREPHTHALATE FROM A METHANOLYSIS VAPOR STREAM

[75] Inventors: Walter E. Toot, Jr., Rochester; Brian L. Simpson, Hamlin, both of N.Y.; Bruce R. Debruin, Kingsport, Tenn.; Andrius A. Naujokas, Webster; William J. Gamble, Rochester, both of N.Y.

[73] Assignee: Eastman Kodak Company, Rochester, N.Y.

[21] Appl. No.: 415,861

[22] Filed: Apr. 3, 1995

[51] Int. Cl.$^6$ .......................... C07C 67/54; C07C 27/28; C07C 29/80
[52] U.S. Cl. .................. 203/6; 203/7; 203/90; 203/94; 203/98; 203/DIG. 23; 560/78; 568/868; 568/871
[58] Field of Search .............................. 203/6, 7, 90, 94, 203/98, DIG. 23; 560/78, 96; 568/868, 871

[56] References Cited

U.S. PATENT DOCUMENTS

| | | | |
|---|---|---|---|
| 2,646,393 | 7/1953 | Hughes et al. | 560/78 |
| 2,793,235 | 5/1957 | Jenkinson | 568/871 |
| 2,828,330 | 3/1958 | Sinn | 203/40 |
| 2,862,021 | 11/1958 | Bille et al. | 203/42 |
| 2,992,168 | 7/1961 | Wilson et al. | 203/69 |
| 3,073,754 | 1/1963 | Aroyan et al. | 560/78 |
| 3,103,470 | 9/1963 | Wilson et al. | 203/69 |
| 3,376,353 | 4/1968 | Tate | 568/871 |
| 3,399,227 | 8/1968 | Tapulionis | 560/78 |
| 3,681,434 | 8/1972 | Neely | 560/98 |
| 4,126,755 | 11/1978 | Bunger et al. | 560/77 |
| 4,760,165 | 7/1988 | Hasegawa et al. | 560/78 |
| 4,776,948 | 11/1988 | Skraba | 203/90 |
| 5,391,263 | 2/1995 | Hepner et al. | 560/78 |

FOREIGN PATENT DOCUMENTS

| | | |
|---|---|---|
| 0225738 | 6/1987 | European Pat. Off. . |
| 2122863 | 12/1971 | Germany . |
| 45-19690 | 7/1970 | Japan . |
| 870012 | 6/1961 | United Kingdom . |
| 872188 | 7/1961 | United Kingdom . |
| 937546 | 9/1963 | United Kingdom . |

Primary Examiner—Robert J. Warden
Assistant Examiner—Robert Carpenter
Attorney, Agent, or Firm—John R. Everett

[57] ABSTRACT

A method of removing dimethyl terephthalate (DMT) from a vapor stream. The vapor stream includes dimethyl terephthalate (DMT), methylhydroxyethyl terephthalate (MHET), glycols and methanol. A distillation column is held under an elevated pressure of 100 to 500 kPag and at a temperature of at least 85° C. It has (i) a plurality of distillation trays; (ii) methanol liquid sprays between the trays; (iii) a main spray zone below the trays and (iv) a liquid pool of methanol in the bottom of the column. The vapor stream is directed into the distillation column, above the liquid pool and below the main spray zone, thereby forming a stream of liquid and vapor. The stream of liquid is directed away from the distillation column walls and into the liquid pool at the bottom of the column. Concurrently, a portion of the liquid in the bottom of the column is (i) recycled back into the distillation column as a spray in the column above the vapor stream inlet, thereby preventing build up of solid DMT on column surfaces and (ii) removed from the column to enable DMT removal.

8 Claims, 1 Drawing Sheet

REMOVAL OF DIMETHYLTEREPHTHALATE FROM A METHANOLYSIS VAPOR STREAM

FIELD OF THE INVENTION

This invention relates to the recovery of dimethylterephthalate (DMT) from a methanolysis reactor that uses excess methanol vapor to remove DMT from the methanolysis reaction mass.

BACKGROUND OF THE INVENTION

In low pressure methanolysis processes for the depolymerization of polyethylene terephthalate, U.S. Pat. No. 5,051,528, a vapor stream carries the volatile reaction products away from the methanolysis reactor. The vapor stream comprises methanol, dimethyl terephthalate (DMT), methyl-2-hydroxyethyl terephthalate (MHET), ethylene glycol, other glycols, acetaldehyde and incompletely reacted polyester components. It is desirable to return as much as possible of the MHET and incompletely reacted polyester components into the reactor. This is accomplished with a fractionation device (rectifier) and heat exchanger (rectifier partial condenser), as described in U.S. Pat. No. 5,298,530. Subsequent to the depolymerization and removal of MHET and other incompletely reacted polyester components, it is desirable to recover and purify the DMT, methanol, and glycols for subsequent use or reuse.

Separating DMT from methanol and glycol, while maintaining desirable yields of DMT, is difficult because of the reactive nature of the DMT and glycol, and the existence of azeotropes. A preferred way to accomplish this separation is to crystallize the DMT in solution containing methanol prior to subsequent purification steps. For crystallization to be most effective, the feed to the crystallizer must be liquid, and the DMT concentration should be in the range of 2–40% weight to weight, with a preferred range of 20–40% weight to weight, and have a minimal amount of acetaldehyde.

The vapor from the methanolysis reactor, rectifier, and rectifier partial condenser must be condensed in order to be fed to a crystallizer. The vapor must also be fractionated because the DMT and acetaldehyde concentrations are not at the preferred concentrations for crystallization. It is preferred to accomplish both the condensation and fractionation in as few devices as possible.

When this condensation and fractionation was attempted on a laboratory scale at atmospheric pressure, and with a surface condenser, the condenser quickly fouled with DMT solids, rendering the system inoperable.

SUMMARY OF THE INVENTION

Figure 1:
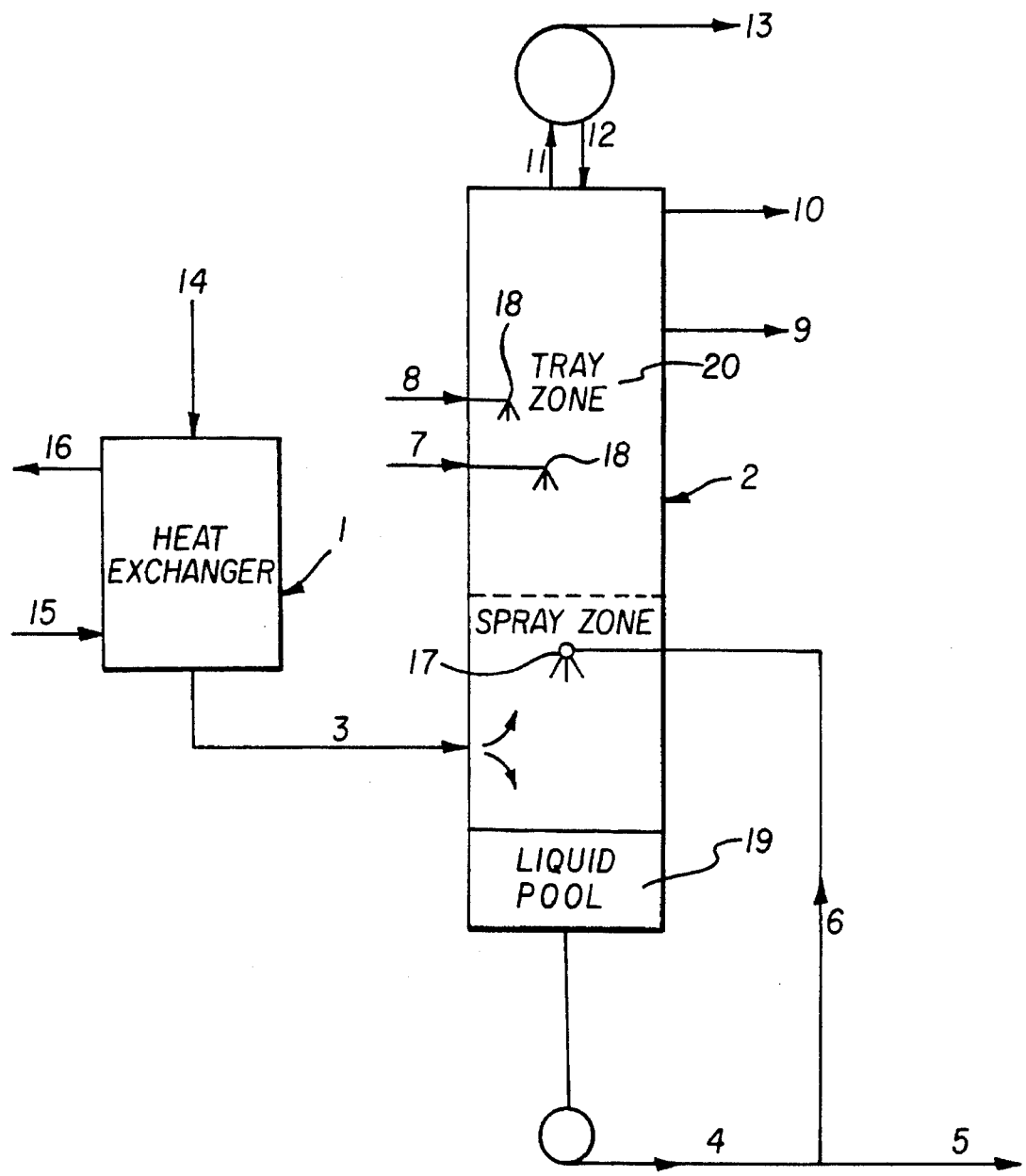
FIG. 1 is a schematic drawing of a distillation column and an optional heat exchanger used in carrying out the process of the invention.

The object of this invention is to prepare DMT solution for subsequent purification and crystallization and avoid fouling of the equipment by solid DMT. This invention achieves this objective with a method of removing dimethyl terephthalate (DMT) from a vapor stream containing a mixture of dimethyl terephthalate (DMT), methylhydroxyethyl terephthalate (MHET), glycols and methanol comprising the steps of:

(a) providing a distillation column that i) is held under an elevated pressure of 100 to 500 kPag and a temperature of at least 85° C. ii) has a plurality of distillation trays iii) has a methanol liquid sprays between the trays iv) has a main spray zone below the trays and v) has a liquid pool comprising methanol at the bottom of the column;

(b) directing the vapor stream through an inlet nozzle into the distillation column above the liquid pool and below the main spray zone thereby forming a liquid solution comprised of vapor stream components;

(c) directing the liquid solution away from the distillation column; and (d) concurrently recycling a portion of the liquid solution from (c) back into the distillation column as a spray in the column above the vapor stream inlet, thereby preventing build up of solid DMT on column surfaces.

In addition to achieving the above objective the invention provides additional advantages of heat economy, methanol purification suitable for reuse, preparation of a liquid solution of DMT suitable for subsequent purification and crystallization, and the removal of low boiling impurities such as acetaldehyde.

DETAILED DESCRIPTION

The following is a detailed description of a representative embodiment of the method of this invention. In the sole FIGURE there are a heat exchanger 1 and a distillation column 2. The use of the heat exchanger is optional. It is not essential to the process. The FIGURE is a schematic representation of these well known devices. Conventional equipment such as pumps, valves, surge drums and the like have been omitted. Use of the latter devices in the schematically described equipment is within the skill of those trained in this art.

A vapor stream comprising a mixture of excess methanol, dimethyl terephthalate (DMT), methyl-2-hydroxyethyl terephthalate (MHET) and glycols is directed into the heat exchanger through line 14. The vapor stream carries the reaction products from a low pressure methanolysis reactor. Methanolysis is a process for the depolymerization of polyethylene terephthalate.

It is necessary to condense the DMT, MHET, glycols and other impurities from the vapor stream into methanol solution, prior to crystallization and subsequent purification of DMT, MHET and other glycols. Crystallization requires the DMT be dissolved in the methanol and be at a certain concentration of about 2 to 60%, preferably 2 to 40% weight percent. We have found 20 to 40% weight percent to be particularly useful.

It is also desirable to separate and simultaneously purify the excess methanol in the vapor stream from the methanolysis reactor. The methanol is suitable for reuse in the methanolysis process.

The optional heat exchanger 1 is constructed according to conventional chemical engineering practice and design for this field. The heat exchanger 1 uses a heat exchange fluid that is supplied at a temperature above the freezing point of the vapor stream mixture and cold enough to partially condense the vapor. The heat exchange fluid has a temperature at the point it enters the heat exchanger through line 15 that is (a) above the freezing point of DMT and (b) low enough to partially condense the vapor stream. Thus, much of the DMT is condensed avoiding any freezing and fouling of the heat exchanger. The selected heat exchange fluid is pumped into the heat exchanger through lines 15. The fluid circulates around the interior of the exchanger for a sufficient time to establish the desired cooling or condensation temperature according to well known design and exits from the heat exchanger through line 16. Suitable heat exchanger fluids include water, and organic heat transfer fluids such as Therminol, p-cymene, dowtherm, paratherm and syltherm.

The heat exchanger partially condenses the vapor stream. The resulting condensate is comprised of dissolved DMT, MHET and glycols. Also, there is some DMT remaining in the vapor state. Most of the methanol remains in the vapor state. The condensate and remaining vapor drains into the distillation column 2 through line 3. Distillation column 2 contains a liquid pool 19 comprising methanol, a plurality of distillation trays in tray zone 20, methanol liquid sprays 18 between the trays and a spray zone 17 below the trays.

The heat exchanger is oriented so that the condensate and vapor mixtures can freely drain into the bottom of distillation column 2. The heat exchange fluid is supplied to the heat exchanger at a high enough temperature so that the condensate and vapor mixtures in line 3 do not freeze. Also, the heat exchange fluid is maintained at low enough temperatures so that the vapors cool and at least partially condense.

The design of distillation column 2 also follows conventional chemical engineering practice. It includes about 10 theoretical plates. The column may use conventional distillation trays, or may be packed with raschig rings, wire mesh or other distillation tower packing materials. Trays are preferred. Special precautions need to be taken in operating the column in order to prevent the trays from becoming dry, which would prevent the column from operating properly. The distillation column includes reflux line 12, and line 11 connected to a heat exchanger.

Pressure inside of the distillation column 2 is maintained high enough to maintain a temperature sufficient to keep DMT in solution in the liquid pool 19, at the bottom of the distillation column 2. The combination of pressure and temperature prevent the formation of solids in the liquid pool. To prevent the formation of DMT solids, the pressure should be maintained in the range of 100 to 500 kPag and sufficient to maintain a temperature of at least 85° C. Preferred temperatures are 85° C. to 127° C., although temperatures above this range will work. The DMT saturated condensate is pumped from the distillation column 2 through lines 4 and 5 to apparatus in which DMT is subjected to further purification, preferably a crystallizer.

As mentioned previously, the stream 3 which issues from the heat exchanger also contains DMT vapors and methanol vapors. These DMT vapors will solidify on any dry surfaces which are below the freezing point temperature of DMT. In order to condense the DMT vapors, it is necessary to subject them to temperatures below the freezing point. Without special measures to prevent dry surfaces, this would ultimately foul the distillation column, similarly to the results observed in the laboratory surface exchanger. To avoid this, a portion of the DMT saturated condensate pumped from the column through lines 4 and 5 is recycled through line 6 into the distillation column as a spray. The spray is directed against the internal walls of the distillation column to prevent DMT vapors from encountering dry surfaces. In addition to this, methanol sprays, 18, are provided between the trays in the trayed section of the distillation column. These sprays are directed against all surfaces including the bottom of the trays and downcomers thereby preventing DMT from encountering any dry surfaces, and fouling the apparatus.

In the distillation column 2, methanol vapors are distilled away from the liquid entering the distillation column through line 3. The methanol vapor rises to the top of the column through the tray zone where it passes through to a heat exchanger through line 11. The methanol is condensed and is returned through the line 12 to the distillation column. The methanol is then pumped out of the column through line 9. Low boiling point impurities, such as acetaldehyde are concentrated and removed through line 10. The remaining methanol thus purified, is available for reuse in the methanolysis process or other processes in which methanol is useful.

The distillation column 2 can also be used to purify a stream containing methanol originating in other parts of a manufacturing facility. Such methanol may contain DMT. Such other methanol streams can be pumped into the column through, for example, lines 7 and 8, where they vaporize and rise to the top of the column along with the methanol which entered through line 3. The methanol is condensed, and pumped out through line 9. Non-condensable gases are removed from the system through line 13.

The invention has been described in detail with particular reference to preferred embodiments thereof, but it will be understood that variations and modifications can be effected within the spirit and scope of the invention.

We claim:

1. A method of removing dimethyl terephthalate (DMT) from a vapor stream containing a mixture of dimethyl terephthalate (DMT), methylhydroxyethyl terephthalate (MHET), glycols and methanol comprising the steps of:

(a) providing a distillation column that i) is held under an elevated pressure of 100 to 500 kPag and a temperature of at least 85° C. ii) has a plurality of distillation trays iii) has methanol liquid spray between the trays iv) has a main spray zone below the trays and v) has a liquid pool comprising methanol at the bottom of the column;

(b) directing the vapor stream through an inlet nozzle into the distillation column above the liquid pool and below the main spray zone thereby partially liquifying the vapor stream containing DMT;

(c) directing the liquid solution away from the distillation column and into the liquid pool at the bottom of the column thereby forming a DMT saturated condensate; and (d) concurrently recycling a portion of the liquid solution from the bottom of the column back into the distillation column as a spray in the column above the vapor stream inlet, thereby preventing build up of solid DMT on column surfaces; and (e) pumping a portion of the liquid pool containing DMT away from the bottom of the condenser for further purification.

2. A method according to claim 1 wherein the vapor stream is fed into a heat exchanger prior to being directed into the distillation column; wherein a heat exchanging fluid has a temperature at the point it enters the heat exchanger that is (a) above the freezing point of DMT and (b) low enough to partially condense the vapor stream.

3. The method of claim 1 wherein methanol is removed from the tray section of the distillation column at a rate sufficient to maintain a DMT concentration in the liquid pool of 20 to 40% weight to weight.

4. The method of claim 1 wherein the methanol liquid spray between the trays comprises methanol liquid from other processing facilities in a manufacturing facility.

5. The method according to claim 4 wherein the methanol liquid spray contains DMT.

6. The method of claim 1 wherein the liquid pool is free of solids.

7. The method of claim 3 wherein the column pressure is adjusted in combination with removal of methanol to maintain the desired concentration of DMT in the liquid pool.

8. The method of claim 7 wherein the liquid pool is free of solids.

\* \* \* \* \*